(12) United States Patent
Chen et al.

(10) Patent No.: US 7,263,396 B2
(45) Date of Patent: Aug. 28, 2007

(54) EAR SENSOR ASSEMBLY

(75) Inventors: Yunquan Chen, Delta (CA); Luya Li, Coquitlam (CA); Rakesh Kumar Sethi, Vancouver (CA); Ming Sun, New Westminster (CA); Christopher Grant Denny, Victoria (CA); Scott Howard Phillips, Victoria (CA)

(73) Assignee: Cardiodigital Limited, East Lothian (GB)

( * ) Notice: Subject to any disclaimer, the term of this patent is extended or adjusted under 35 U.S.C. 154(b) by 289 days.

(21) Appl. No.: 10/900,146

(22) Filed: Jul. 28, 2004

(65) Prior Publication Data

US 2005/0033131 A1 Feb. 10, 2005

Related U.S. Application Data

(60) Provisional application No. 60/493,361, filed on Aug. 8, 2003.

(51) Int. Cl.
*A61B 5/00* (2006.01)
(52) U.S. Cl. ............... 600/340; 600/344

(58) Field of Classification Search ............... 600/322, 600/323, 340, 344
See application file for complete search history.

(56) References Cited

U.S. PATENT DOCUMENTS

| | | | |
|---|---|---|---|
| 5,237,997 A | | 8/1993 | Greubel et al. |
| 5,551,423 A | * | 9/1996 | Sugiura ............... 600/323 |
| 5,611,337 A | | 3/1997 | Bukta |
| 6,080,110 A | | 6/2000 | Thorgersen |
| 6,556,852 B1 | * | 4/2003 | Schulze et al. ......... 600/323 |
| 6,675,031 B1 | * | 1/2004 | Porges et al. ........... 600/322 |
| 2005/0015018 A1 | * | 1/2005 | Dolphin et al. ......... 600/559 |

FOREIGN PATENT DOCUMENTS

WO  WO 00/53094  * 9/2000

* cited by examiner

*Primary Examiner*—Eric Winakur
*Assistant Examiner*—Etsub Berhanu
(74) *Attorney, Agent, or Firm*—Oyen Wiggs Green & Mutala LLP

(57) ABSTRACT

A sensor assembly for monitoring physiological characteristics interfaces to a subject's ear. The sensor assembly has a projection that projects into the subject's concha. The projection may have a notch to accommodate the subject's anti-tragus. A clip connected to the projection holds a sensor against the subject's lobule. The sensor may comprise a pulse-oximetry-type sensor.

10 Claims, 15 Drawing Sheets

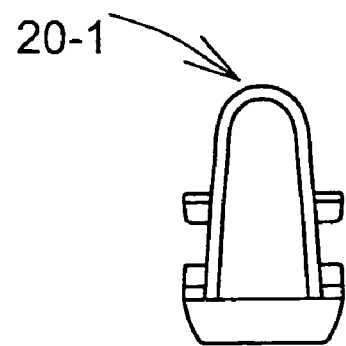
FIGURE 9C
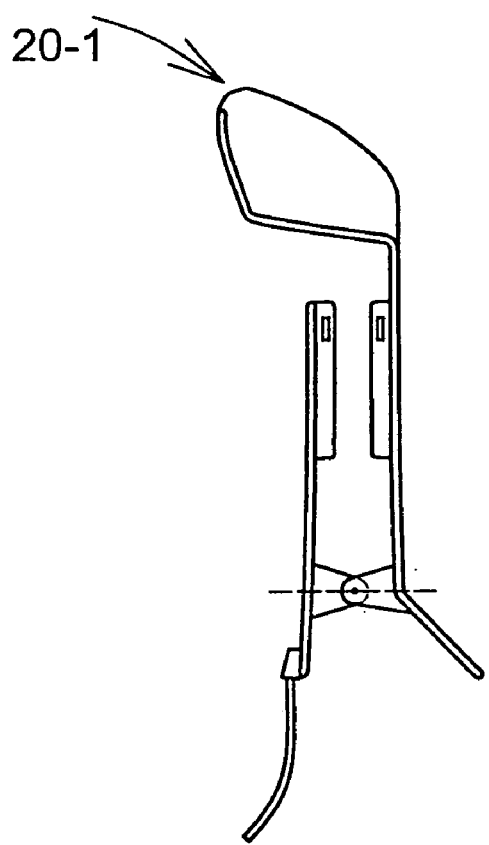
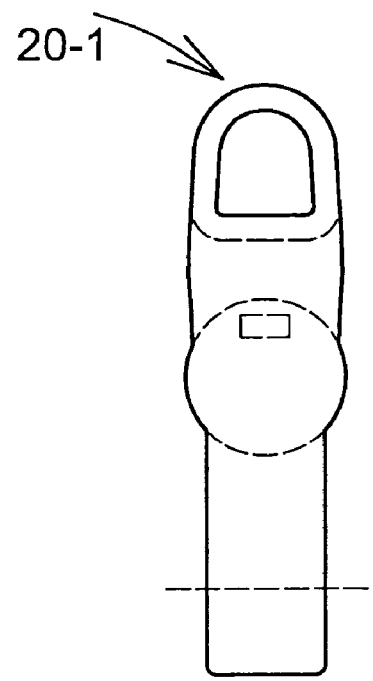
FIGURE 9A  FIGURE 9B

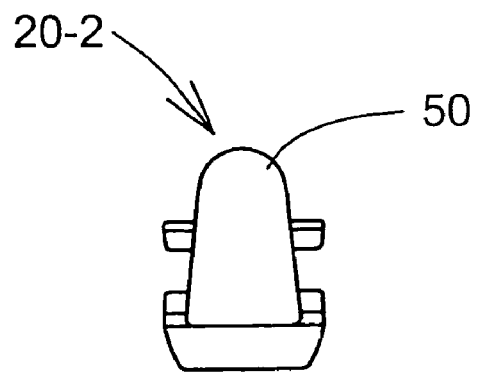
FIGURE 10C
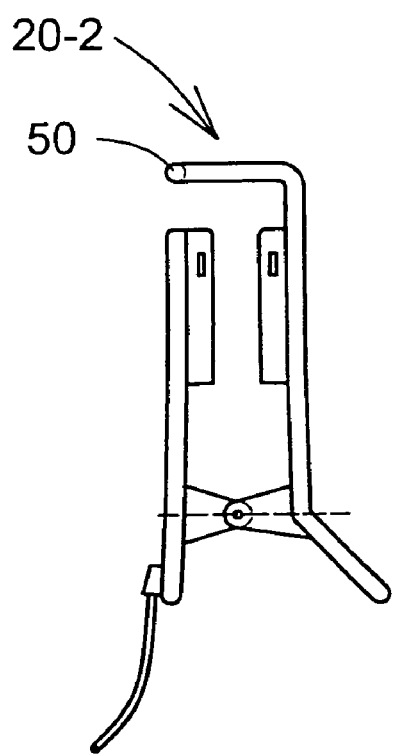
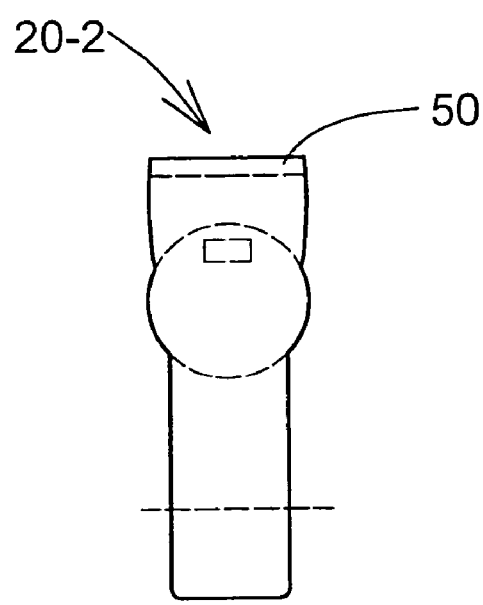
FIGURE 10A     FIGURE 10B

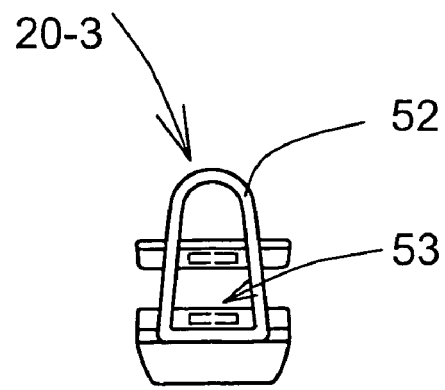
FIGURE 11C
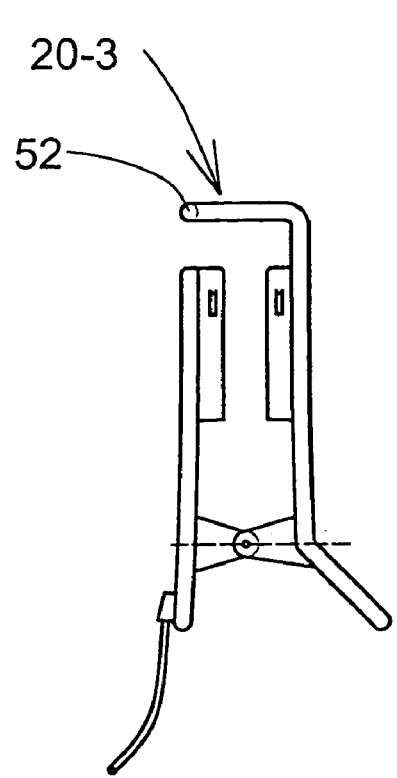
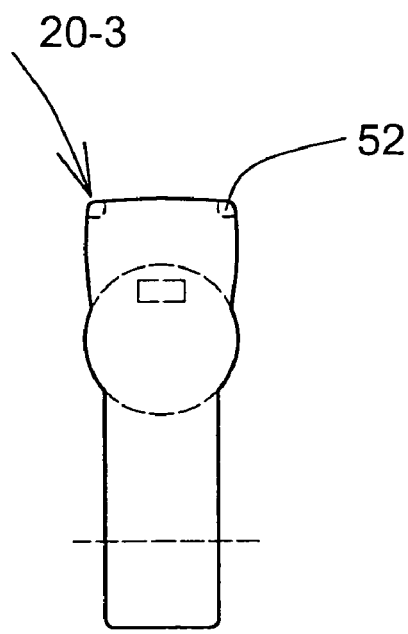
FIGURE 11A  FIGURE 11B

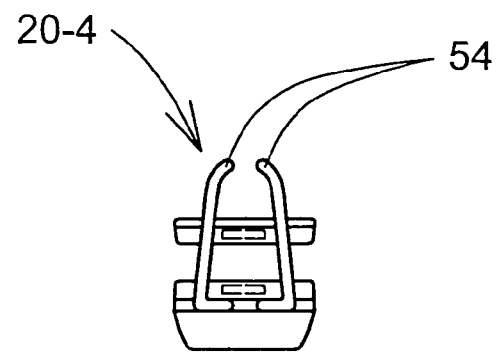
FIGURE 12C
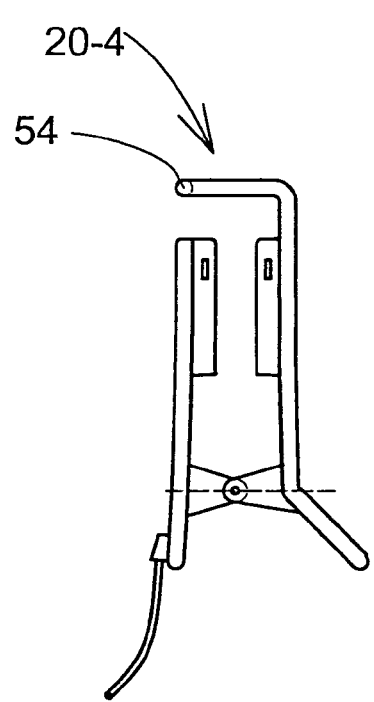 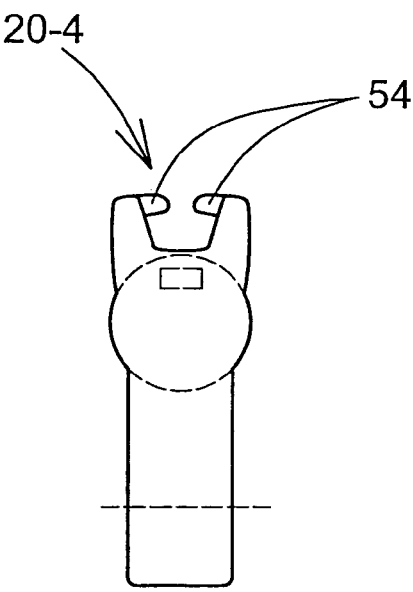
FIGURE 12A     FIGURE 12B

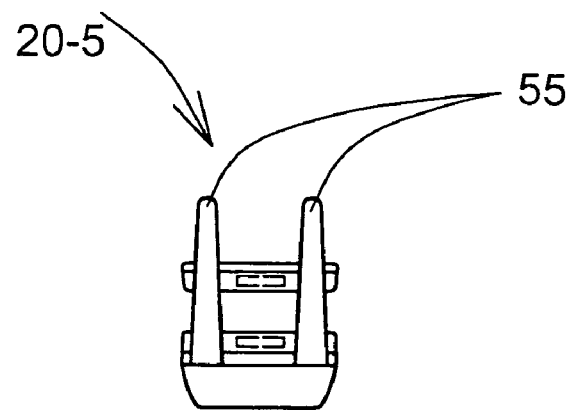
FIGURE 13C
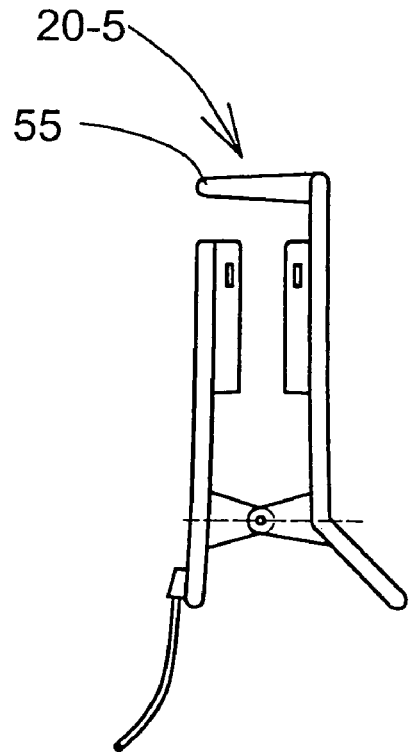
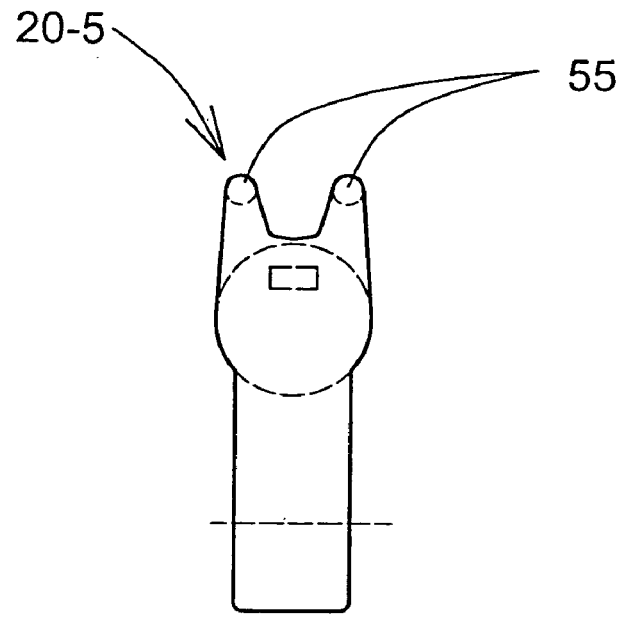
FIGURE 13A  FIGURE 13B

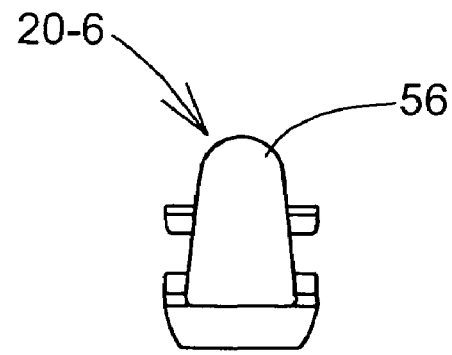
FIGURE 14C
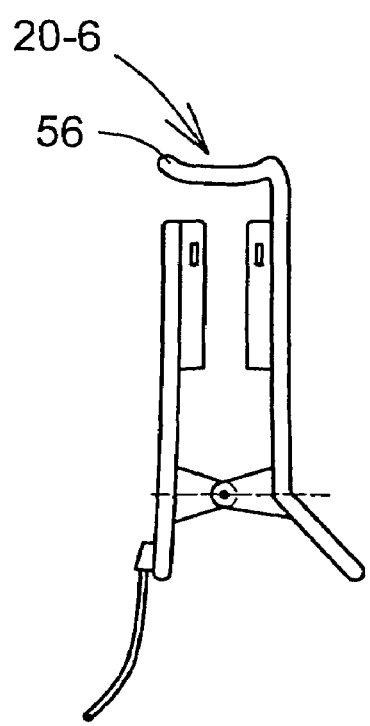 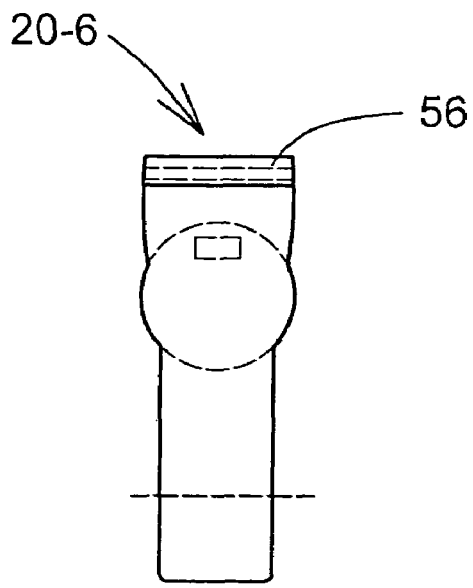
FIGURE 14A   FIGURE 14B

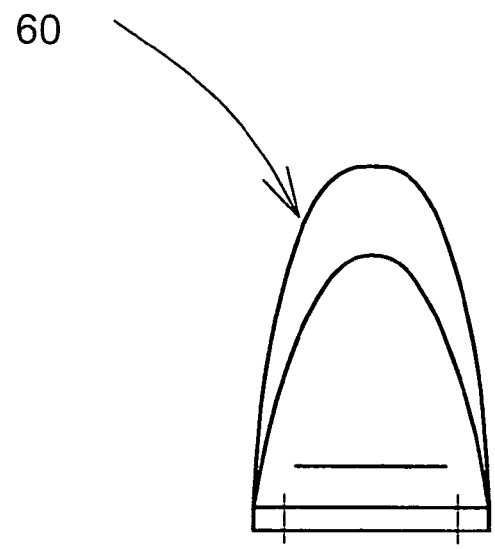
FIGURE 15C
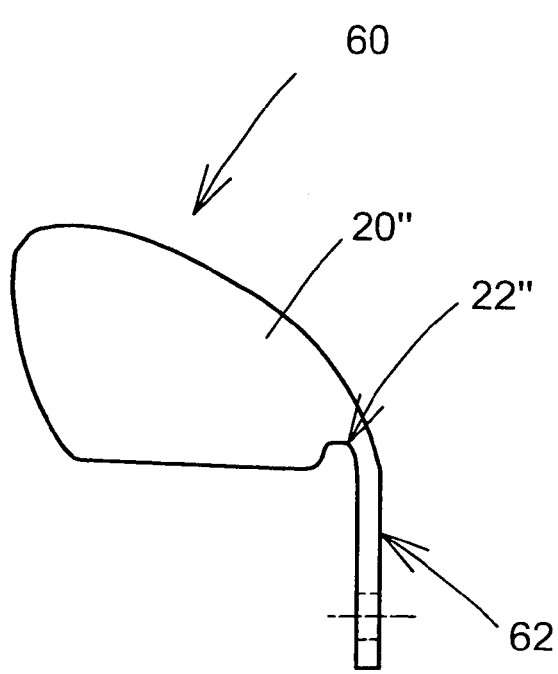 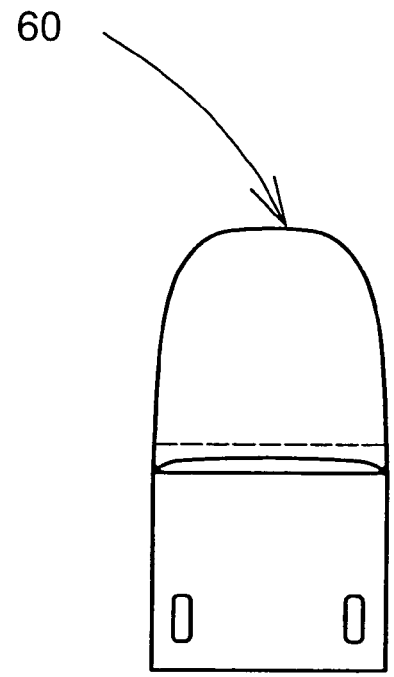
FIGURE 15A FIGURE 15B

EAR SENSOR ASSEMBLY

CROSS REFERENCE TO RELATED APPLICATION

This application claims the benefit of U.S. application No. 60/493,361 filed on 8 Aug. 2003.

TECHNICAL FIELD

The invention relates to physiological sensors which interface to a subject's ear.

BACKGROUND

There are various circumstances in the health care field where it is desirable to measure some physiological characteristic of a subject person and it is convenient to make such measurement using a sensor which interfaces to the subject's ear.

For example, some known pulse oximetry sensors clip to a subject's earlobe. An example of one such pulse oximetry sensor is described in Bukta, U.S. Pat. No. 5,611,337. An example of a heart rate sensor which clips onto a subject's earlobe is shown in FIG. 3 of Greubel et al., U.S. Pat. No. 5,237,997. Various types of sensors may be clipped to a subject's earlobe. The output signals of such sensors may be used for various purposes including measuring heart rate, measuring blood oxygen saturation, measuring blood pressure, measuring temperature, or the like.

Clipping a sensor to a subject's earlobe is convenient. However, the inventors have identified a number of disadvantages of current earlobe sensors. These include the following:

Some sensors work best when located in a specific position on a subject's earlobe. A typical ear sensor can be clipped onto a subject's ear in different locations. It can be difficult to repeatedly find the position in which such a sensor works best. In some cases, it is necessary to try several times before a satisfactory output signal can be obtained.

Earlobe clips can be pulled off with relative ease.

Current earlobe sensors do not always stay fixed on a subject's ear but may move over time relative to a desired sensing location. This can cause the quality and fidelity of the sensor output signals to vary over time. Movements of the sensors may themselves create artifacts in the sensor output signals, further degrading output signal quality and fidelity.

Some sensors are designed to be inserted into a subject's ear canal. Thorgersen, U.S. Pat. No. 6,080,110 describes such a sensor. Such sensors have the disadvantages that they occlude the subject's ear canal and can be uncomfortable if kept in place for too long.

There is a need for ear sensors which ameliorate at least some of the disadvantages of current ear sensors. There is a particular need for ear sensors capable of generating quality, robust and stable pulse signals at a subject's ear.

SUMMARY OF THE INVENTION

The invention relates to methods and apparatus for obtaining signals, such as pulse signal, from a sensor which interfaces to the ear of a subject. The sensor is held in place in a sensor assembly which includes a projection. The projection extends into the concha of a subject's ear.

One aspect of the invention provides an ear sensor assembly. The ear sensor assembly comprises a projection insertable into the concha of a subject's ear and a clip connected to the projection. The clip comprises a first part biased toward a second part. The ear sensor assembly comprises a sensor on at least one of the first and second parts of the clip. The sensor assembly may comprise a pulse-oximetry-type sensor, for example.

Another aspect of the invention provides an ear sensor assembly comprising a sensor holder. The sensor holder includes a projection insertable into a subject's concha and a clip located to grasp a lobule of the subject's ear when the projection is inserted into the concha. The sensor assembly also comprises a sensor supported by the sensor holder. The sensor is located to sense a physiological characteristic, for example a pulse signal at a location on the subject's ear.

Another aspect of the invention provides an ear sensor comprising grasping means for grasping a subject's ear, the grasping means including sensor support means for supporting a sensor in a location proximate a lobule of the subject's ear; and, holding means for preventing the grasping means from slipping off the subject's ear, the holding means are connected to the grasping means. The grasping means, sensor support means and holding means may have any of the various structures described herein as well as equivalents thereof.

Further aspects of the invention and features of specific embodiments of the invention are described below.

BRIEF DESCRIPTION OF THE DRAWINGS

In drawings which illustrate non-limiting embodiments of the invention,

FIGS. 9A through 14C illustrate various alternative configurations for projections of sensor assemblies according to embodiments of the invention;

FIGS. 15A, 15B and 15C are respectively a side elevation, a front elevation and a bottom plan view of a part that may be added to a conventional clip-on sensor assembly to provide a sensor assembly according to the invention.

DESCRIPTION

Throughout the following description, specific details are set forth in order to provide a more thorough understanding of the invention. However, the invention may be practiced without these particulars. In some cases, well known elements have not been shown or described in detail to avoid unnecessarily obscuring the invention. Accordingly, the specification and drawings are to be regarded in an illustrative, rather than a restrictive, sense.

This invention provides ear sensor assemblies. An ear sensor assembly according to the invention has a grasping portion that grasps a subject's ear, typically on the subject's earlobe, and a holder portion which projects into the concha of the subject's ear. The holder portion may help to accurately locate the sensor, to resist forces which could otherwise undesirably pull or knock the sensor assembly off of the subject's ear, and/or to retain the sensor assembly so that the sensor stays in a desired position relative to the subject's ear.

Figure 1:
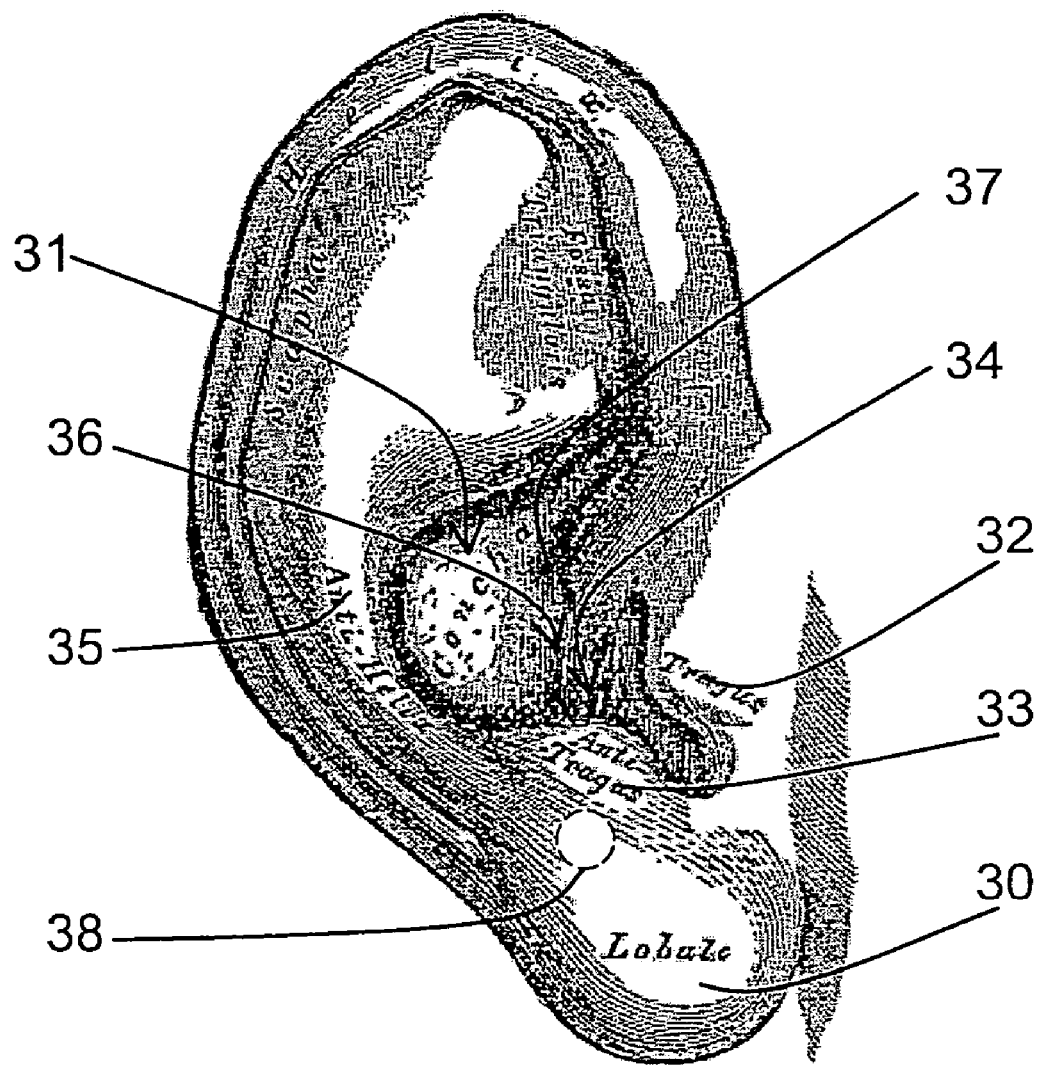
FIG. 1 is a view of the outer ear showing a preferred location for a pulse-oximetry-type sensor.

FIG. 1 shows a human outer ear. The ear has a downwardly-descending lobule 30 which extends upwardly to just below the rim of a concha 31. A tragus 32 and an anti-tragus 33 project over concha 31. The inter-tragic incisure 34 is a portion of the ear which extends along the rim of concha 31 and separates tragus 32 from anti-tragus 33. The antihelix 35 is a portion of the ear which extends along the rim of concha 31 posterior to anti-tragus 33. The inferior portion 36 of concha 31 is called the cavum conchae. Concha 31 has an inferior wall 37. Wall 37 typically extends more or less in a plane which is roughly perpendicular to lobule 30.

Figure 2:
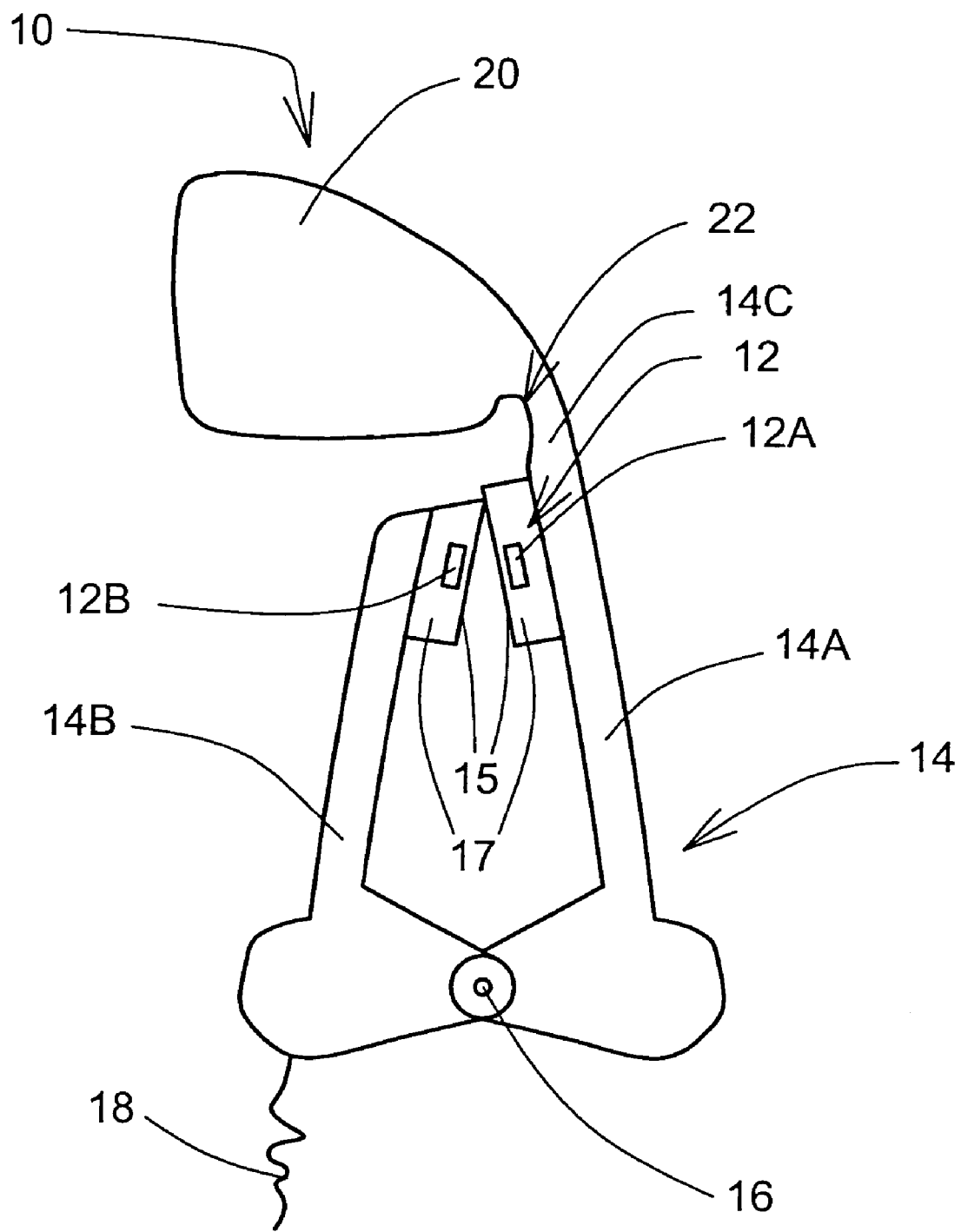
FIG. 2 is a side view of a sensor assembly according to one embodiment of the invention.

FIG. 2 shows a sensor assembly 10 according to an illustrative embodiment of the invention. Sensor assembly 10 comprises a sensor 12. In the illustrated embodiment, sensor 12 has two parts. A first part 12A is intended to contact the lateral side of a subject's earlobe. A second part 12B is intended to contact the medial side of the subject's earlobe. Parts 12A and 12B may provide mechanisms for making any of a variety of types of physiological measurements. For example, sensor 12 may be a transmission type pulse oximetry sensor in which one of parts 12A, 12B transmits optical radiation at one or more wavelengths and the other one of parts 12A, 12B receives the optical radiation after it has passed through a portion of the subject's outer ear.

The inventors have determined that a region 38 of lobule 30 close to anti-tragus 33 is particularly good for detecting pulse signals using a pulse-oximetry type sensor. In preferred embodiments of the invention, sensor assembly 10 holds sensor 12 in contact with region 38 of a subject's ear. The invention is not limited to such embodiments, however. In some embodiments a notch 22 accommodates the anti-tragus and helps hold sensor assembly 10 in a desired position on a subject's ear.

Parts 12A and 12B are mounted on opposed arms of a U-shaped clip 14. Clip 14 presses sensor parts 12A and 12B toward one another. In the illustrated embodiment, clip 14 comprises an outer part 14A which carries sensor part 12A and an inner part 14B which carries part 12B. Clip parts 14A and 14B are coupled together by a hinge which includes pin 16. A spring (not shown) or other suitable bias means biases sensor parts 12A and 12B toward one another. As clip 14 performs the function of grasping the subject's ear, clip 14 may be termed a grasping means. As outer part 14A and/or inner part 14B perform the function of supporting sensor parts (12A and 12B), the parts may be termed sensor support means.

Clip 14 provides ear-contacting surfaces 15. In the illustrated embodiment, ear-contacting surfaces 15 are outer surfaces of pads 17 which are disposed on clip parts 14A and 14B away from hinge pin 16. Sensor parts 12A and 12B are disposed within pads 17. A cable 18 provides a path for carrying signals to and from sensor 12. Cable 18 may carry conductors for supplying driving current to one or more light sources of sensor 12 and conductors for carrying signals from sensor 12 to a control unit (not shown).

A projection 20 is coupled to clip 14. In the illustrated embodiment, projection 20 projects in an inward direction from an end 14C of outer clip part 14A. Projection 20 is located and dimensioned to project into the concha of a subject's ear when sensor 12 is in a desired position on a subject's ear. The desired position coincides with region 38 (see FIG. 1) in some embodiments. A lower face of projection 20 projects at an angle of approximately 90 degrees±20 degrees to a plane of sensor 12. As projection 20 serves the function of better holding ear sensor assembly 10 to a subject's ear, projection 20 may be termed a holding means.

Figure 3:
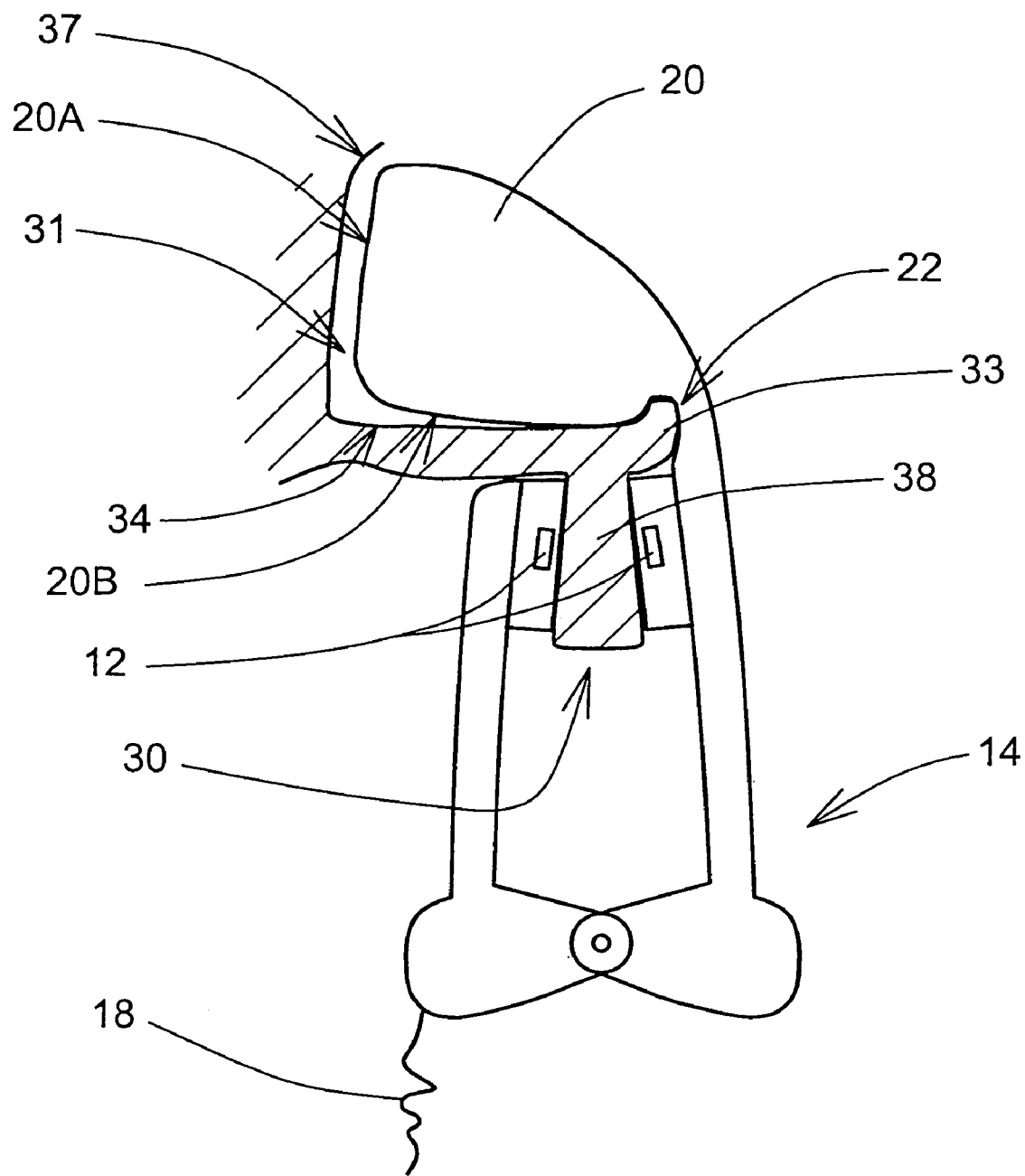
FIG. 3 is a cross section of the sensor assembly of FIG. 2 in place on a subject's ear.
Figure 4:
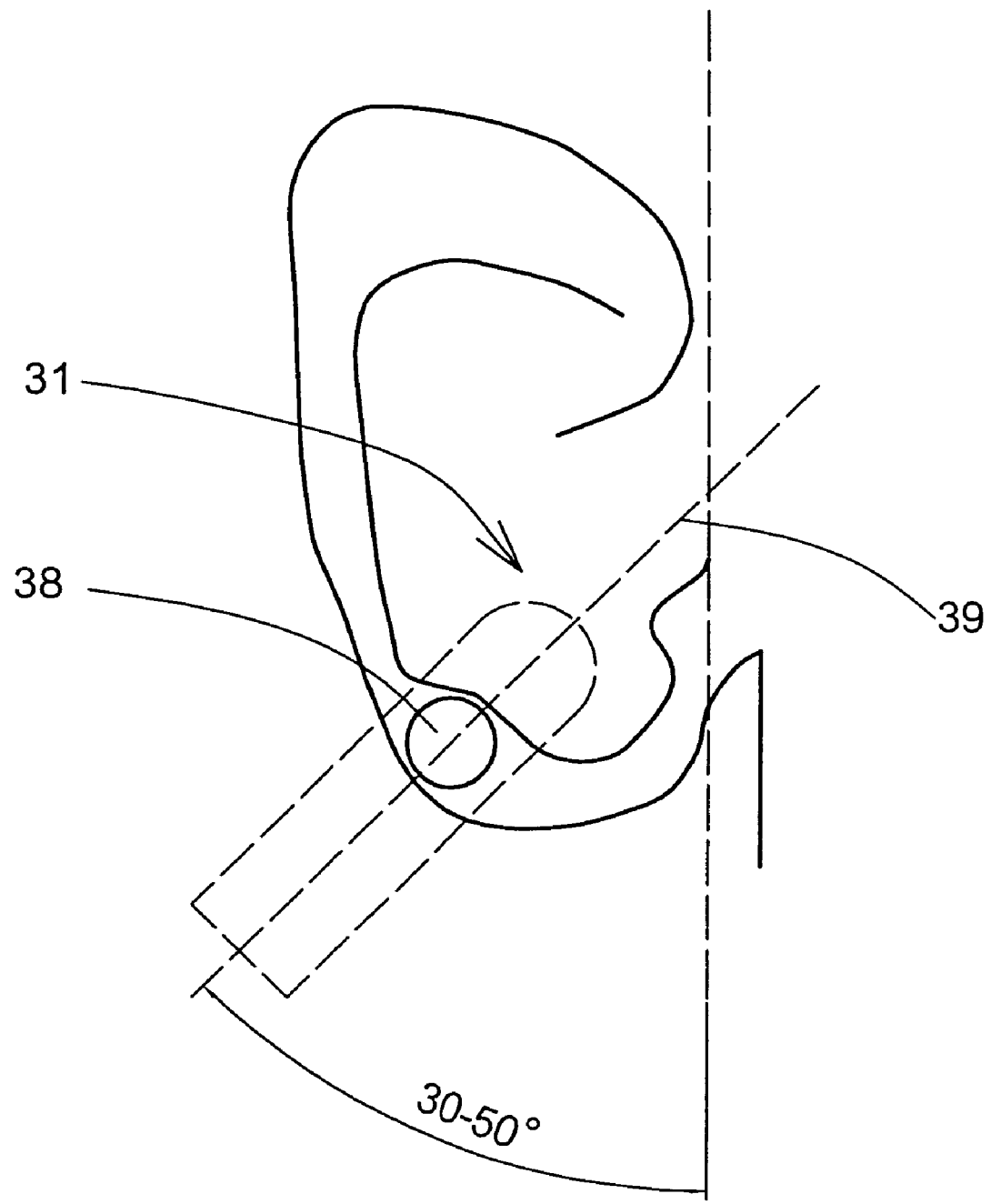
FIG. 4 is a side elevation view of the sensor assembly of FIG. 2 in place on a subject's ear.
Figure 5:
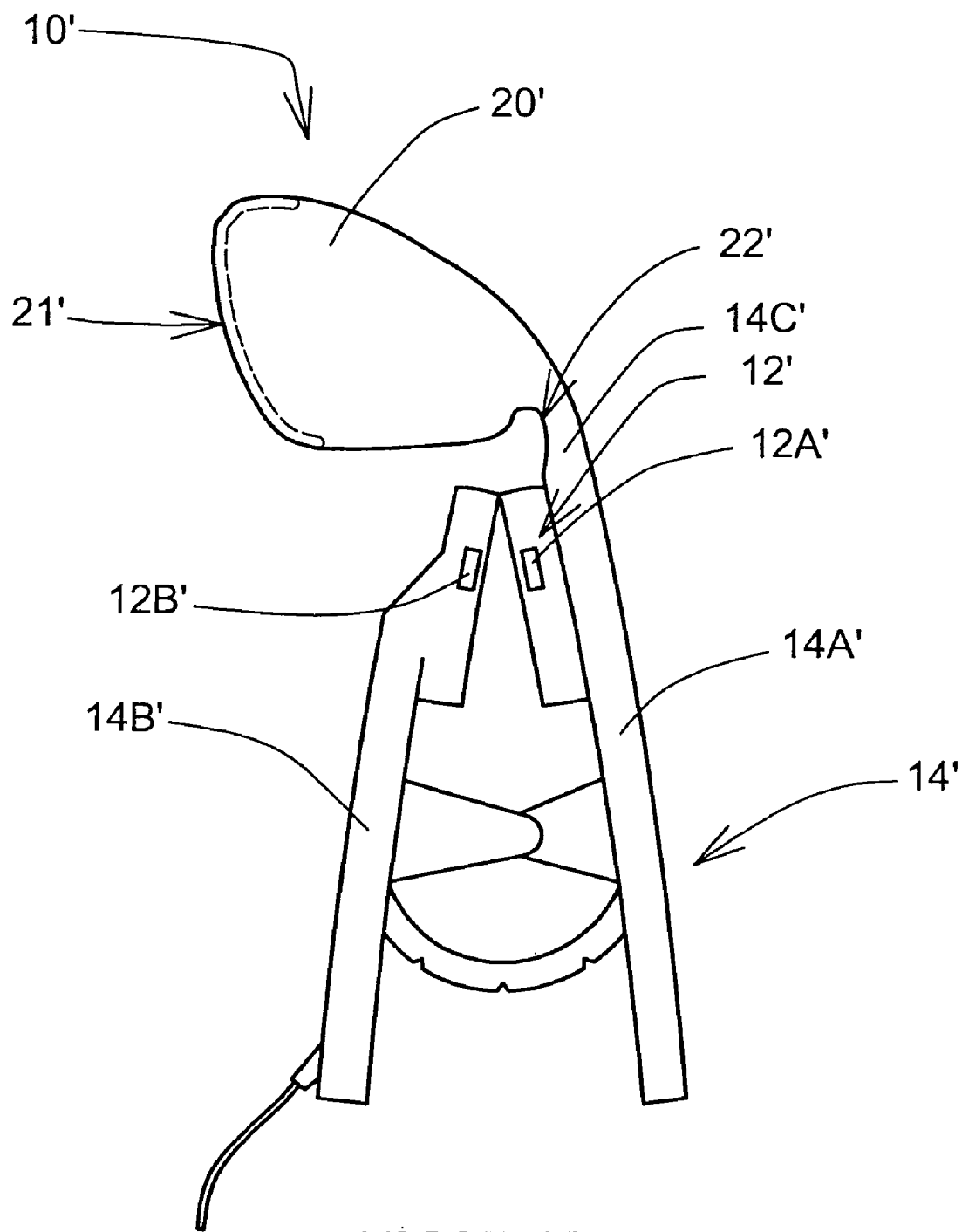
FIG. 5 is an isometric view of a sensor assembly according to an alternative embodiment of the invention.
Figure 6:
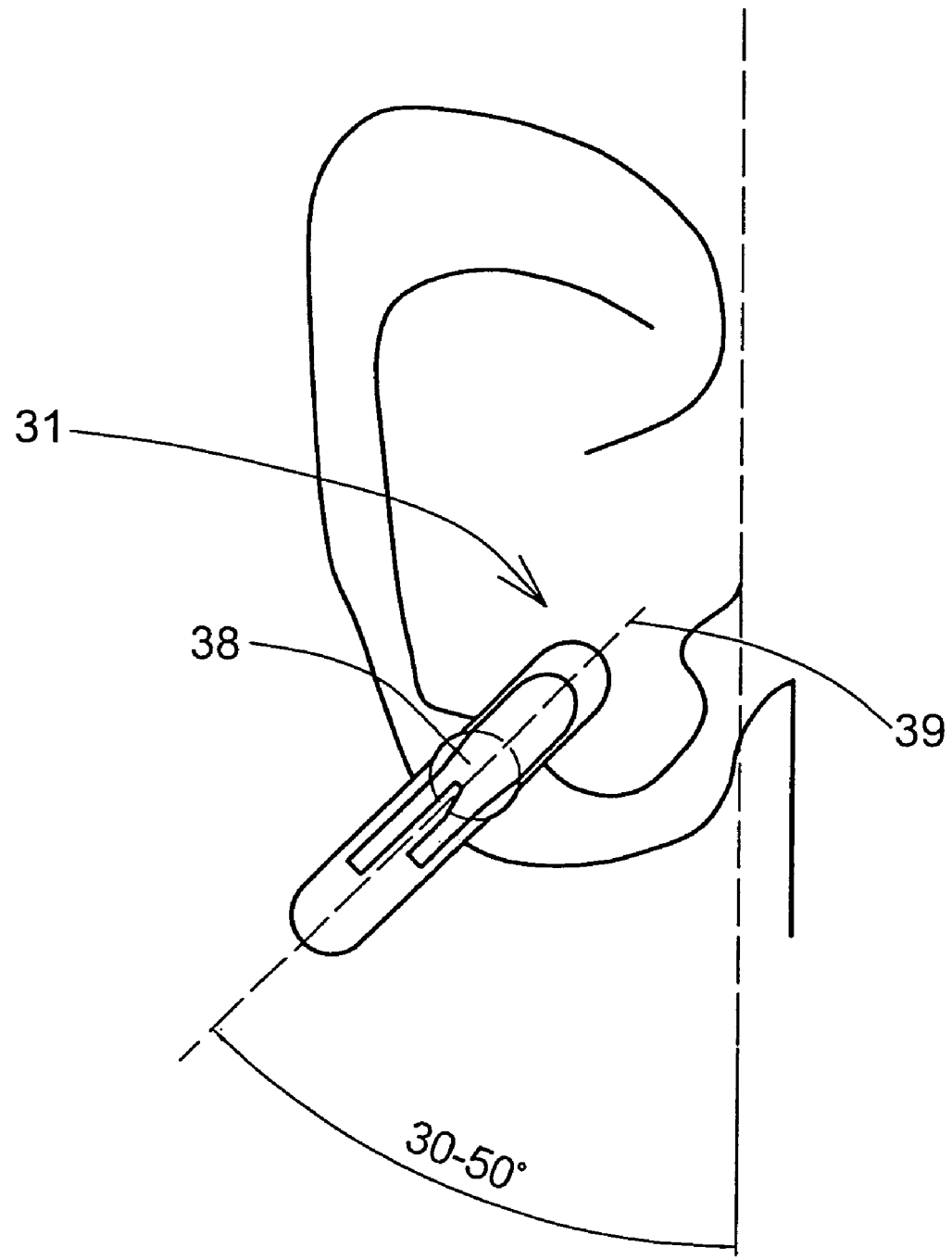
FIG. 6 is a side elevation view of the sensor of FIG. 5 in place in a subject's ear.
Figure 7:
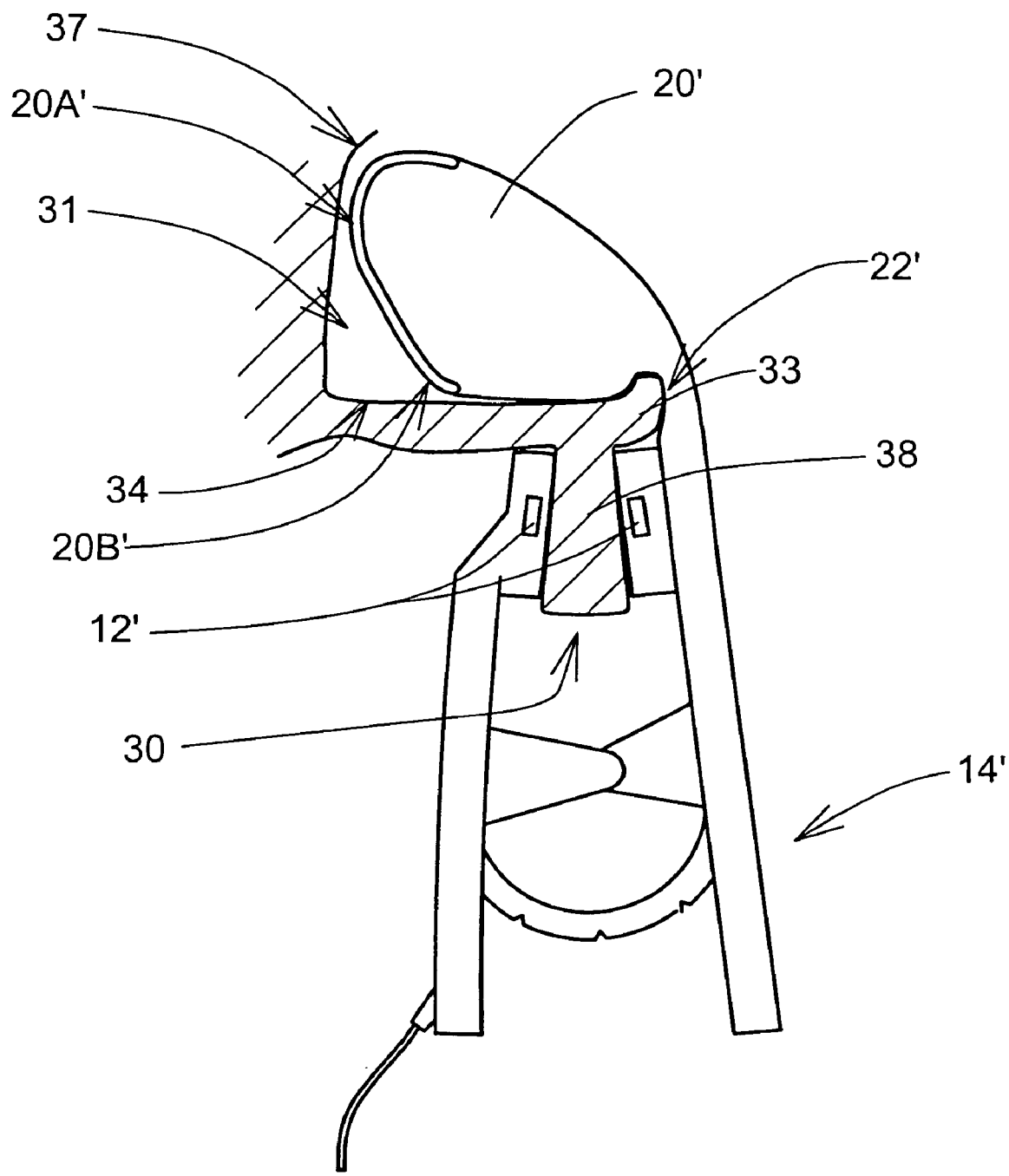
FIG. 7 is a cross sectional view of the sensor of FIG. 5 in place in a subject's ear.
Figure 8:
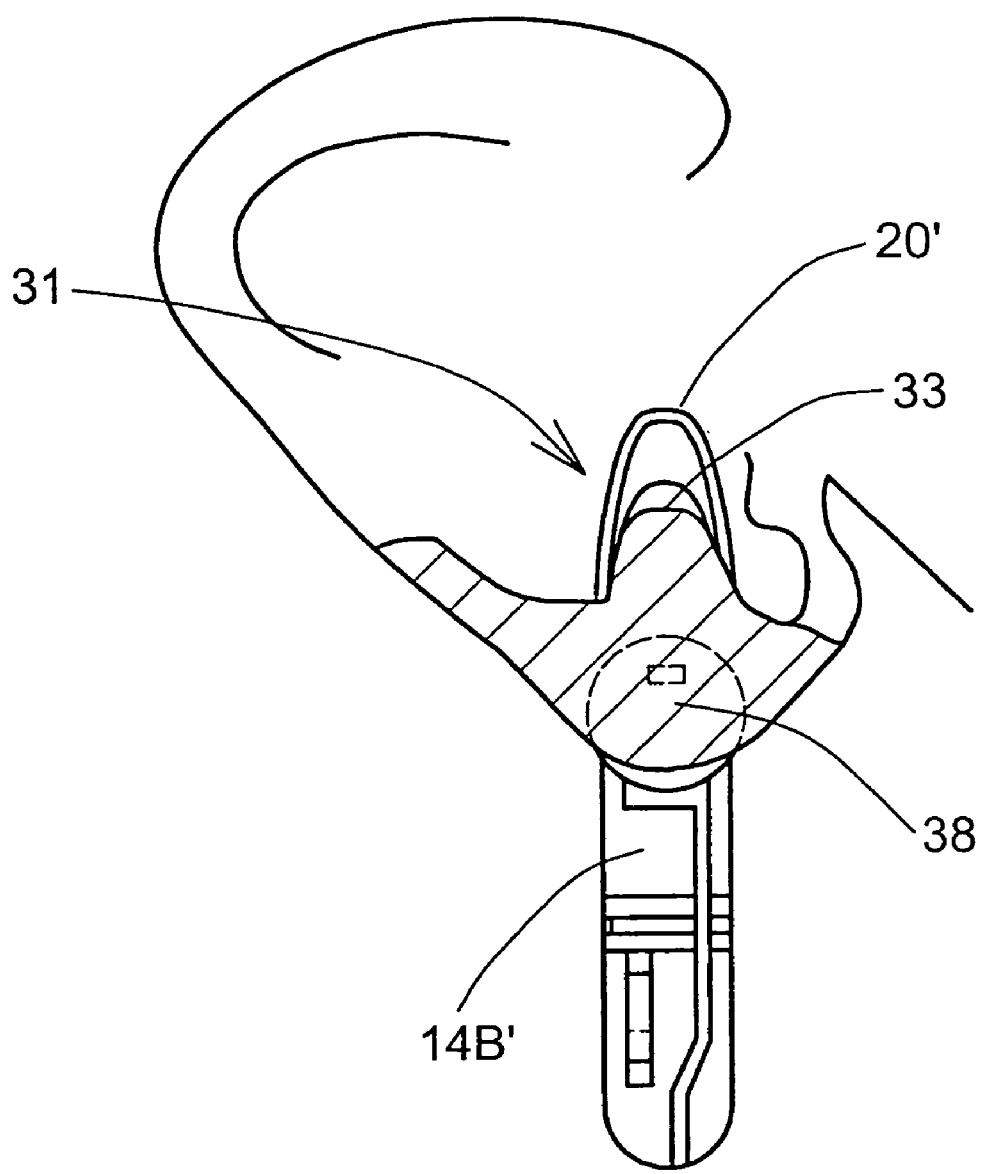
FIG. 8 is another cross sectional view (in a plane medially displaced from the cross section plane of FIG. 7) of the sensor of FIG. 5 in place in a subject's ear.

FIGS. 3 and 4 show sensor assembly 10 in position on a subject's ear. It can be seen that clip 14 positions sensor 12 over region 38. Sensor parts 12A and 12B press against opposed sides of the subject's lobule 30. Projection 20 projects into the subject's concha 31 and contacts wall 37. A forward-projecting member 25, (shown in dotted outline in FIG. 4) may optionally be provided to prevent sensor assembly 10 from slipping toward the subject's face. Another member 25 may project from the other side of clip 14 for use when the sensor assembly is being used on the subject's other ear.

As shown in FIG. 3, sensor assembly 10 has a notch 22 at the intersection of projection 20 and clip 14. Notch 22 accommodates the subject's anti-tragus 33. A lower face 20A of projection 20 contacts wall 37. A side face 20B may be shaped to contact the portion of the wall of the concha which is adjacent to inter-tragic incisure 34. The shaped side face of projection 20 may have a convex curvature, though it is not limited to this shape. Projection 20 projects inwardly into the subject's concha past outer sensor part 12A and preferably past inner sensor 12B. In some embodiments, projection 20 projects inward a distance in the range of 7 mm to 14 mm from the plane of the outside of the subject's lobule 30 (i.e. a plane passing through the face of outer sensor part 12A).

As shown in FIG. 4, a line 39 extending between the center of region 38 and the part of concha 31 closest to the center of region 38 is typically at an angle of 30° to 50° to the vertical (with vertical referenced to the subject's head).

Sensor assembly 10 may be symmetrical, as shown in FIG. 2, in which case it may be used with either a subject's right or left ear. In this case, an axis of symmetry 24 of sensor assembly 10 may be oriented so that it extends generally along line 39 when the sensor assembly 10 is properly in place on a subject's ear.

The ear-contacting surfaces of sensor portions 12A and 12B and projection 20 may be made of, or coated with, material which provides a high coefficient of friction with the skin of the ear. The high-friction material may be on a replaceable cover or may be a part of sensor assembly 10 not intended to be removed in normal use. The high-friction material may comprise, for example, rubber, silicone, another suitable elastomer, or the like. The high-friction material may comprise an elastomer having a tacky surface.

The ear-contacting surfaces of sensor assembly 10 may be significantly larger than required for operation of sensor 12 to provide large contact areas with inner and outer surfaces of lobule 30. Sensor portions 12A and 12B may be offset toward projection 20 in the ear-contacting portions so that they line up with region 38.

FIGS. 5 through 8 show a sensor assembly 10' according to an alternative embodiment of the invention. In FIGS. 5 through 8, features of sensor assembly 10' which correspond to features of the sensor assembly 10 depicted in FIGS. 2, 3 and 4 are identified by the same reference numerals as are used in FIGS. 2, 3 and 4, modified by the addition of a "prime" symbol—'. Sensor assembly 10' differs from sensor assembly 10 primarily in that projection 20' is apertured. In the illustrated embodiment, projection 20' comprises a partial ring, specifically a projecting half-ring 21'. Half-ring 21' may be coated with a material having a high coefficient of friction. In some example embodiments, half-ring 21' has a radius in the range of 3.5 mm to 6 mm. In some example embodiments, half-ring 21', has a thickness in the range of about 1.5 mm to 3 mm.

There are many alternative configurations for projection 20. Some possible alternative configurations are shown in FIGS. 9A through 14C. FIGS. 9A, 9B and 9C show a projection 20-1 which is similar to the projection 20 shown in FIG. 1 except that some non-ear-contacting surfaces are cut away. FIGS. 10A, 10B and 10C show a projection 20-2 which comprises a generally flat panel 50 projecting inwardly from clip 14. Panel 50 may have a rounded triangular shape as shown. FIGS. 11A, 11B and 11C show a projection 20-3 which comprises a generally flat panel 52 penetrated by an aperture 53. A projection may comprise two or more projection members, one or more of which extends into the concha of a subject's ear. FIGS. 12A, 12B and 12C show a projection 20-4 which comprises a pair of curved pin projection members 54. In some example embodiments the curved pin projection members 54 have lengths in the range of 8 mm to 16 mm. FIGS. 13A, 13B and 13C show a projection 20-5 comprising a pair of straight pin projection members 55. In some example embodiments, pin projection members 55 have lengths in the range of 6 mm to 9 mm. FIGS. 14A, 14B and 14C show a projection 20-6 which is similar to projection 20-2 except that it is convex on its bottom side 56.

Projection 20 may be formed as a unitary part with at least the outer part 14A of clip 14, e.g. in an injection molding process. In the alternative, projection 20 and outer part 14B of clip 14 may be assembled from two or more smaller parts. In one embodiment, sensor assembly 10 is assembled by attaching a projection 20 to an existing clip-on ear sensor. FIGS. 15A, 15B and 15C show an example of a part 60 which includes a projection 20" on an arm 62. Part 60 may be attached to a suitable conventional clip-on ear sensor using a suitable adhesive, welding, or in any other suitable manner to provide a sensor assembly according to the invention.

Where a component (e.g. an assembly, device, sensor etc.) is referred to herein, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

As will be apparent to those skilled in the art in the light of the foregoing disclosure, many alterations and modifications are possible in the practice of this invention without departing from the spirit or scope thereof. For example,
Sensor assemblies according to the invention may include
    single-part sensors in addition to, or instead of, the two-part sensors described above.
Sensor assemblies according to the invention may include
    sensors with any number of parts or any number of means of detecting physiological characteristics, mounted on
    either or both sides of clip 14.
Instead of coupling clip parts 14A and 14B with a hinge
    defined by a pin 16, as shown in FIG. 2, parts 14A and
    14B could be connected by a section of material which is
    flexible enough to permit parts 14A and 14B to be moved
    toward and away from one another. In such embodiments,
    the section of material may itself be resilient so as to serve
    as a means for pressing parts 14A and 14B toward one
    another.
A sensor assembly according to the invention may be
    asymmetrical. Different sensor assemblies may be provided for use on left and right ears.
Projection 20 could be coupled to the rest of the sensor
    assembly in such a way as to allow movement (for
    example, pivoting) relative to the sensor assembly. The
    projection 20 could be movable between a first position
    for use in a subject's left ear and a second position for use
    in a subject's right ear.

The scope of the invention is defined by the following claims.

What is claimed is:

1. An ear sensor assembly comprising:
    a projection insertable into the concha of a subject's ear;
    a clip connected to the projection, the clip comprising a first part biased toward a second part; and
    a sensor on the first part of the clip,
    wherein one end of the second part is connected to the first part, a second end of the second part is movable toward and away from the first part, the projection projects from the first part; and
    wherein the projection is penetrated by an aperture and comprises a portion of a ring and the portion of a ring has a radius in the range of 3.5mm to 6mm and a thickness in the range of 1.5mm to 3mm.

2. An ear sensor assembly according to claim 1 wherein a sensor is on the second part of the clip.

3. An ear sensor assembly according to claim 1 wherein the first and second parts of the clip are hingedly connected to one another.

4. An ear sensor assembly according to claim 1 wherein the first and second parts of the clip are coupled together by a resilient member, and the resilient member biases the second end of the second member toward the first member.

5. An ear sensor assembly according to claim 1 wherein the projection comprises a half-ring.

6. An ear sensor assembly according to claim 1 wherein the projection has a surface characterized by a high coefficient of friction with human skin.

7. An ear sensor assembly according to claim 1 comprising a removable cover on the projection.

8. An ear sensor assembly according to claim 7 wherein the removable cover comprises an elastomeric material.

9. An ear sensor assembly according to claim 1 wherein the sensor comprises a first component on the first part of the clip and a second component on the second part of the clip.

10. An ear sensor assembly according to claim 9 wherein one of the first and second components emits radiation and another one of the first and second components receives the radiation.

\* \* \* \* \*